(12) United States Patent
Krishnapuram et al.

(10) Patent No.: US 7,892,831 B2
(45) Date of Patent: Feb. 22, 2011

(54) **METHOD FOR IN VITRO MASS CULTURE OF *ALOE VERA***

(76) Inventors: Sreenivasachar Murali Krishnapuram, Reliance Life Sciences Pvt. Ltd., DALC, Plot No. R-282 TTC Area of MIDC, Rabale, Navi Mumbai, Maharashtra (IN) 400 701; Neera Pandey, Reliance Life Sciences Pvt. Ltd., DALC, Plot No. R-282 TTC Area of MIDC, Rabale, Navi Mumbai, Maharashtra (IN) 400 701

( * ) Notice: Subject to any disclaimer, the term of this patent is extended or adjusted under 35 U.S.C. 154(b) by 61 days.

(21) Appl. No.: 12/295,168

(22) PCT Filed: Mar. 30, 2007

(86) PCT No.: PCT/IN2007/000134
§ 371 (c)(1),
(2), (4) Date: Sep. 29, 2008

(87) PCT Pub. No.: WO2008/007389
PCT Pub. Date: Jan. 17, 2008

(65) Prior Publication Data
US 2009/0249511 A1 Oct. 1, 2009

(30) Foreign Application Priority Data
Mar. 31, 2006 (IN) .................. 488/MUM/2006

(51) Int. Cl.
*C12N 5/00* (2006.01)
*C12N 5/02* (2006.01)

(52) U.S. Cl. ............. 435/410; 435/420; 435/430; 435/430.1; 435/431

(58) Field of Classification Search ............... 435/410, 435/420, 430, 430.1, 431
See application file for complete search history.

(56) References Cited

U.S. PATENT DOCUMENTS
2006/0015963 A1 * 1/2006 Neera et al. ............... 800/278

FOREIGN PATENT DOCUMENTS
CN 1276423 A 12/2000
DE 10032108 A1 1/2002

OTHER PUBLICATIONS

Aggarwal et al. "Tissue Culture Propagation of Elite plant of *Aloe vera* Linn," J. Plant Biochemistry and Biotechnology vol. 13, pp. 77-79, Jan. 2004.*
Abrie et al. "Micropropagation of the endangered *Aloe polyphylla*," Plant Growth Regulation, 33: 19-23, 2001.*
Natali et al. "In vitro culture of *Aloe barbadensis* Mill.: Micropropagation from vegetative meristems," Plant, Cell, Tissue and Organ Culture 20: 71-74, 1990.*
Turner et al. "Evaluation and comparison of commercially available Aloe vera L. products using size exclusion chromatography with refractive index and multi-angle laser light scattering detection," International Immunopharmacology 4 (2004) 1727-1737.*
Meyer et al., "Rapid In Vitro Propagation of *Aloe-barbadensis* Mill", Plant Cell, Tissue & Organ Culture, 26(3):167-172 (1991).
Roy et al., "In Vitro Regeneration and Micropropagation of *Aloe Vera* L.", Scientia Horticulturae, 47(1-2):107-114 (1991).
Sanchez et al., "In Vitro Culture of *Aloe Barbadensis* Mill.: Morphogenetic Ability and Nuclear DNA Content", Plant Science, 55(1):53-59 (1988).
Velcheva et al., "Regeneration of *Aloe arborescens* via somatic organogenesis from young inflorescences", Plant Cell, Tissue & Organ Culture, 83(3):293-301 (2005).

* cited by examiner

*Primary Examiner*—Susan B McCormick Ewoldt
(74) *Attorney, Agent, or Firm*—Mintz Levin Cohn Ferris Glovsky and Popeo, P.C.; Ivor R. Elrifi; Christina K. Stock, Esq.

(57) ABSTRACT

The present invention provides a method for producing a true-to-type clone of an *Aloe barbadensis* mother plant by selecting an *Aloe barbadensis* mother plant; isolating a meristematic explant from the plant; culturing the meristematic explant in initiation medium to generate shoots, where the media lacks hormones; culturing the shoots in proliferation and elongation medium to generate elongated shoots, where the proliferation and elongation media comprises benzyl adenine (BA) and indole butyric acid (IBA); culturing the elongated shoots in rooting medium to generate plantlets, where the media lacks hormones; and culturing the plantlets to product a true-to-type clone of the *Aloe barbadensis* mother plant.

7 Claims, 2 Drawing Sheets

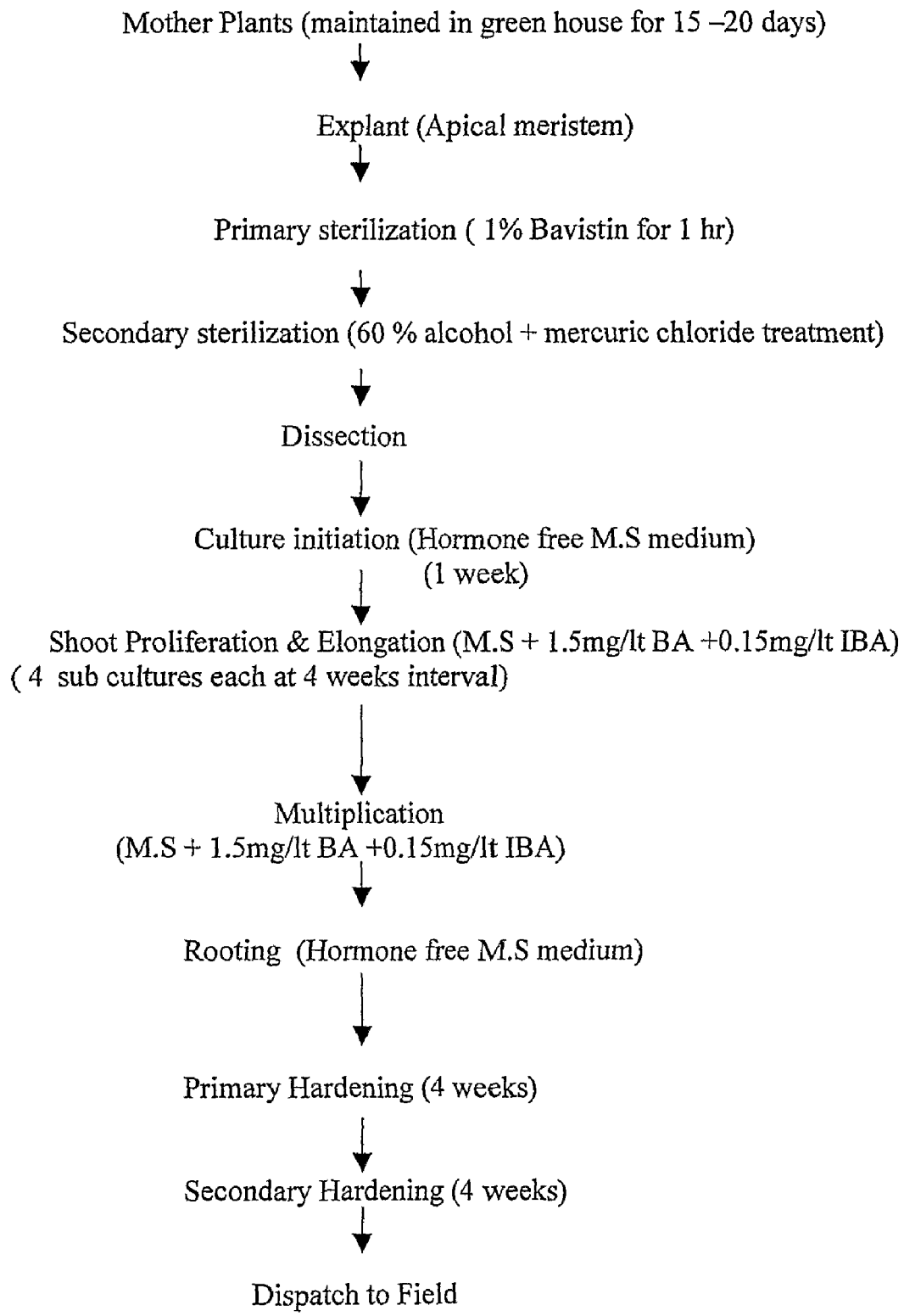
FIGURE 1: Flow Sheet for Micropropagation of Aloe Vera

Figure 2 : Initiation
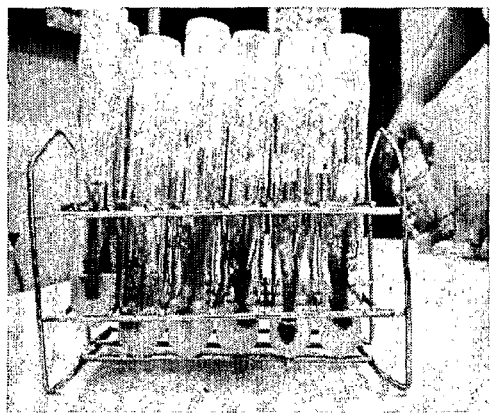
Figure 3: Multiplications
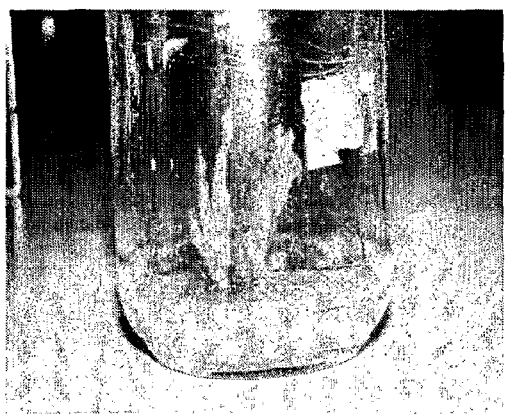
Figure 4: Rooting
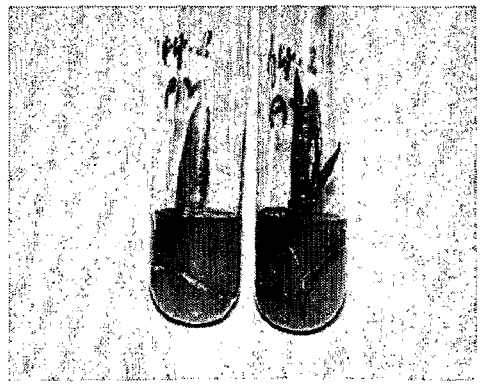

METHOD FOR IN VITRO MASS CULTURE OF *ALOE VERA*

CROSS-REFERENCES TO RELATED APPLICATIONS

This application claims benefit of provisional Indian Application No. 488/MUM/2006, filed Mar. 31, 2006, which is hereby entirely incorporated by reference.

FIELD OF THE INVENTION

The present invention relates to a method for in vitro micropropagation of *Aloe vera* (syn. *A. barbadensis*). The invention in particular relates to a commercially viable process for in vitro mass culture.

BACKGROUND INFORMATION

Aloe, native to East and South Africa, is also known as 'Lily of the desert', 'Plant of immortality', and 'The medicine plant'. *Aloe barbadensis* was introduced to the West Indies at the beginning of the 16th century.

*Aloe vera* (*Aloe barbadensis*), is a member of the Liliaceae family and is an evergreen perennial growing to 0.8 m by 1 m at a slow rate. It is in leaf all year and in flower from May to June. The flowers are hermaphroditic (having both male and female organs).

The plant prefers sandy or medium loamy, well-drained soil and can grow in nutritionally poor soil. It cannot grow in shade. It can grow in dry or moist soil and can tolerate drought. In gardens the plant needs some protection from winter cold.

Seeds are usually sown during the spring season in a greenhouse. Seeds usually germinate in 1-6 months at 25° C. One should place the seedlings in individual pots of very well drained soil when they are large enough to handle and grow them in a sunny part of the greenhouse for at least the first two winters. If the plants are to be planted outdoors, they should be planted in early summer to allow them to become established before the winter and to give them some protection from the cold. The plants produce offsets quite freely and they can be divided at any time of the year as long as long as it is warm enough to encourage fresh root growth to allow re-establishment of the plants.

*Aloe vera* leaf contains major glycoside-anthracene derivatives such as hydroxy anthraquinone derivatives (25-40) namely, aloin, barbaloin (a mixture of aloin A & B), the diastereoisomeric 10-C glucosides of aloe-emodin anthrone and 7-hydroxyaloin isomers. Minor components also include aloe emodin, chrysophanol, chromone derivatives, namely, aloeresin B (=aloesin, up to 30%) with its p-coumaryl derivatives aloeresins A & C and the aglycone aloesone. The active component of aloe is a mixture of glycosides called aloin. The proportion of aloin varies in different specimens of aloes. The chief constituent of aloin is barbaloin, which is a pale yellow crystalline glycoside, soluble in water.

Uses for *Aloe vera*

*Aloe vera* is a fairly well known herbal preparation with a long history of use. It is widely used in modern herbal practice and is often available in proprietary herbal preparations. It has two distinct types of medicinal uses:

1) The clear gel contained within the leaf makes an excellent treatment for wounds, burns and other skin disorders by placing a protective coat over the affected area, speeding up the rate of healing and reducing the risk of infection. This action is in part due to the presence of Aloectin B, which stimulates the immune system. To obtain this gel, the leaves can be cut in half along their length and the inner pulp rubbed over the affected area of skin. This has an immediate soothing effect on all sorts of burns and other skin problems.

2) The second use comes from the yellow sap at the base of the leaf. The leaves are cut transversally at their base and the liquid that exudes from this cut is dried. It is called bitter aloes and contains anthraquinones which are a useful digestive stimulant and a strong laxative.

The plant is useful as a emmenagogue, emollient, laxative, purgative, stimulant, stomachic, tonic, vermifuge and vulnerary. Extracts of the plant have antibacterial activity.

Apart from its external use on the skin, *Aloe vera* (usually the bitter aloes) is also taken internally in the treatment of chronic constipation, poor appetite, digestive problems etc.

*Aloe vera* should not be given to pregnant women or people with hemorrhoids or irritable bowel syndrome. The plant is strongly purgative so great care should be taken to adjust the dosage properly. The plant is used to test if there is blood in the feces. This plant has a folk history of treatment in cases of cancer. Other uses include cosmetic products employing leaf extracts of aloe.

Plants have been grown indoors in pots in order to help remove toxins from the atmosphere. The plant is unusual in that it continues to release oxygen and absorb carbon dioxide in the dark, making it very suitable for growing in living rooms.

The cathartic action of the *Aloe vera* is attributed to the anthraquinone glycosides, chiefly aloin.

Commercial preparations of creams, lotions, shampoos and allied products such as gel of aloe are used as it has a cooling effect and acts as a moisturizing agent.

Given the above-described useful properties of aloe, there is a large demand for the aloe plants. The present invention helps to satisfy this demand by providing a means for in vitro micropropagation of *Aloe vera* which is economical and can produce on a commercial scale true-to-type elite variety, disease-free Aloe vera plants of uniform quality.

*Aloe vera* Plant Tissue Culture

Micropropagation is the in vitro regeneration of plants from organs, tissues, cells or protoplast using techniques like tissue culture for developing true-to-type resultant plants of a selected genotype. In general, tissue from a plant commonly known as an explant is isolated from a plant whose multiplication is desired to create a sterile tissue culture of that species in vitro. From explants a culture is initiated. Once a culture is stabilized and growing well in vitro, multiplication of the tissue or regeneration of entire plant can be carried out. Shoots (tips, nodes or internodes) and leaf pieces are commonly used but cultures can be generated from many different tissues. Juvenile tissues generally respond best. Besides the source of the explants, the chemical composition of the culture medium and the physical environment of cultures have been found to be of a great influence on the regeneration capacity, multiplication ratio, growth and development of new plants in the culture system. Therefore, one needs to optimize these factors for individual plant species.

Plant tissue culture is rapidly becoming a commercial method for large-scale propagation of the elite varieties, particularly for plants which are difficult to propagate rapidly by conventional methods. Tissue culture is particularly useful for multiplication of plants which are slow-growing (turmeric, ginger, cardamom); cross-pollinated (coconut, teak, eucalyptus, cashew, mango and those which show wide variation in the progeny), male sterile lines (cotton, sorghum, pearl millet); and newly free plants by meristem culture (sugarcane, potatoes, tapioca, etc).

There is a need in the art for micropropagation methods for aloe that have high shoot ratios (for example, each plant gives 4 plants after 4 weeks i.e., 1:4 multi rate) and high survival rates up to the hardening stage.

SUMMARY OF THE INVENTION

The present invention addresses the problems encountered in micropropagation of *Aloe vera*.

In one aspect, the invention provides methods for producing true-to-type clones of *Aloe barbadensis* mother plants by selecting an *Aloe barbadensis* mother plant; isolating a meristematic explant from the plant; culturing the meristematic explant in initiation medium to generate shoots, where the initiation medium lacks hormones; culturing the shoots in proliferation and elongation medium to generate elongated shoots, where the proliferation and elongation media comprises benzyl adenine (BA) and indole butyric acid (IBA); culturing the elongated shoots in rooting medium to generate plantlets, where the rooting medium lacks hormones; and culturing the plantlets to produce a true-to-type clone of the *Aloe barbadensis* mother plant.

In preferred embodiments, the *Aloe barbadensis* mother plant is an elite variety, preferably one having a high acemmanan content.

In preferred embodiments, proliferation and elongation media contains benzyl adenine at a concentration ranging from 1.5 to 3 mg/L, preferably 1.5 mg/L, 2 mg/L, 2.5 mg/L, or 3 mg/L; and most preferably at 1.5 mg/L.

In other preferred embodiments, the indole butyric acid is at a concentration of about 0.15 mg/L, about 0.5 mg/L, about 1 mg/L, about 2 mg/L, and about 3 mg/L; most preferably about 0.15 mg/L.

In still other preferred embodiments, the meristematic explant is from a shoot tip or a nodal bud. Preferably, the shoot tip has bud tissue; most preferably, apical bud tissue.

BRIEF DESCRIPTION OF THE FIGURES

The following drawings form the part of the present invention and are included to substantiate and demonstrate the important aspects of the disclosure. The present invention may be better understood by the following drawings in combination with the detailed description of the specific embodiments presented herein.

FIG. 1 shows a flow sheet for an embodiment of the micropropagation method of this invention.

FIG. 2 shows initiation of an apical bud.

FIGS. 3*a* and *b* show an *Aloe vera* culture with multiple shoots from a single explant.

FIG. 4 shows shoots with roots.

DETAILED DESCRIPTION OF THE INVENTION

Definitions

The term "micropropagation" as used herein refers to the in vitro regeneration of plants from organs, tissues, cells or protoplasts and the true-to-type propagation of a selected genotype using in vitro culture technique.

The term "callus" as used herein refers to an unorganized or undifferentiated mass of proliferative cells produced either in culture or in nature.

The term "true-to type propagation" as used herein means that all characteristics present in mother plant will also be present in next generation, i.e., the plantlets will be the true type of the mother plant.

The term "fungicide" as used herein means any chemical substance that destroys and inhibits the growth of fungi.

The term "insecticide" as used herein means any substance, synthetic or organic, which inhibits, kills, or destroys insects.

The term "MS" as used herein refers to Murashige and Skoog's medium.

The term "IBA" as used herein refers to Indole-3-butyric acid.

The term "FYM" as used herein refers to farm yard manure which can be like compost.

The term "M-45" as used herein refers to Dithane M-45.

The term "BAP" as used herein refers to 6-benzyl amino purine.

The term "BA" as used herein refers to benzyl adenine.

General

The present invention provides a process for in vitro mass culture of *Aloe vera* that allows production of true-to-type Aloe vera plants, where the process involves micropropagation of the explants in initiation medium and rooting medium lacking hormones and proliferation and elongation media containing benzyl adenine and indole butyric acid.

In some embodiments, the process has steps including, but not limited to, selecting the healthy mother plant, treating the mother plant, isolating an explant, cleaning the explants with detergent solution, sterilizing the explants by primary and secondary sterilization, inoculating the explants on culture initiation medium, transferring the cultures to proliferation and elongation medium, transferring the elongated shoots to rooting medium, subjecting in vitro grown plantlets to primary and secondary hardening, and transferring the hardened plantlets to the field.

Selection of Mother Plant

The mother plant can be any type of *Aloe vera* plant of an elite variety or standard variety.

In preferred embodiments, mother plants having high acemannan levels are selected for isolation of explants. Such plants are tested for high acemannan content using standard methods known to those of skill in the art, such as lyophilization and assay with NMR. By way of example, the leaf layer is cut and the mucilage gel (which will be a transparent, odorless gelly substance) is removed. This gel is mixed with some antioxidants and preservatives, filtered enough to remove the debris, and then frozen. This liquid extract of *Aloe vera* gel is used for lyophilisation and subject to NMR analysis.

The preferred level of acemannan depends on the particular variety of *Aloe vera* and the location of cultivation. There is specific preferred concentration. As a plant's acemannan level will depend upon both the genotypic and phenotypic character, it differs from clone to clone. We have tested acemannan level in the following plants:

| Variety | Source | Acemannan Percentage |
| --- | --- | --- |
| *Aloe barbadensis* | Florida USA | 10.6% |
| *Aloe barbadensis* | Florida USA | 9.9% |
| *Aloe barbadensis* | Florida USA | 12.1% |

Preparation of the Mother Plant

In certain embodiments, the mother plant from which the explants are harvested is subject to screening to identify healthy specimens and/or treatment to either maintain a disease-free state or to treat existing disease.

Health can be determined by assessing the plants for their size, weight, general growth, appearance, and absence of infection or contamination.

Decontamination can be performed by spraying the plants with agents such as fungicides, insecticides, pesticides or the like. Preferred fungicides for the pretreatment of the mother plant include Bavistin™, Captan™, Dithane™, Thiram™, Thiovit™, or combinations thereof at a concentration of about 0.05% to 0.2%. Preferred insecticides for the pretreatment of the mother plant include, but are not limited to, Rogor™, Nuvacron, Fastac™, Ultracid™ 40-WP, Thiodane™ at a concentration of about 0.005% to 0.02%.

Explants

The present invention provides a method for efficient in vitro mass culture of *Aloe vera* using explants from meristematic tissue. Since meristematic cells are undifferentiated, the use of such tissue as an explant allows regeneration of true-to-type clones of the mother plants.

In preferred embodiments, shoot tip or nodal buds are used as explants. In the most preferred embodiments, the contemplated explant is shoot tip with bud tissue. Apical meristem bud tissue is particularly preferred, as it is an active part of the plant and relatively contamination free.

Preferably, the explant used in the present invention is selected from healthy, fresh, disease-free plants. The explants, may be isolated from mother plants growing in various locations, both wild and cultivated.

Preparation of the Explants for Culture

Cleaning of Explants

In some embodiments, the explants are cleaned prior to inoculation in the media. Cleaning is performed using methods known to those of skill in the art, for example, by shaking explants in a mild detergent, such as Tween-20.

Sterilization of Explants

In other embodiments, the explants are sterilized prior to inoculation in the media. Sterilization can be performed using any method known to those of skill in the art, for example, by treatment with fungicide, a surface sterilizing agent, or combinations thereof. The explant may be subjected to a single round of sterilization or multiple rounds of sterilization.

For example, the explant may go through a primary sterilization step with the fungicide Bavistin and then go through a secondary sterilization with a surface sterilizing agent like sodium hypochlorite or mercuric chloride.

Culture of Explants

The present invention provides a method for efficient in vitro mass culture of *Aloe vera* using meristematic explants and culture in media with specific hormone compositions. Other aspects of the micropropagation process can be performed using methods known to those of skill in the art in plant tissue culture. Micropropagation typically involves the following steps: 1) culturing explants in initiation media to generate multiple shoots; 2) transferring shoots to proliferation and elongation media; 3) transferring the elongated shoots to rooting media; 4) hardening the plantlets, and 5) transferring the hardened plantlets to fields.

The basal media used to culture *Aloe vera* can be any of those already known in the field of the art for plant tissue culture, such as Murashige & Skoog, Gamborg's, Vacin & Went, White's, Schenk & Hildebrandt or the like.

Basal media can also be supplemented with various carbon sources. The carbon source may be sucrose or glucose, typically, at a concentration of about 2-5%. The carbon source may also be sugar alcohol like myo-inositol, typically, at a concentration of about 50-500 mg per liter.

In some embodiments, the basal media will include gelling agents such as agar, alginic acid, carrageenan, and gellangum. Typical concentrations are 0.5-1%.

Phytohormones in Media

The present invention provides for a method where meristematic explants are grown in initiation and rooting media lacking hormones and proliferation and elongation media containing benzyl adenine and indole butyric acid The media may also contain phytohormones in addition to those than those listed above.

The phytohormones present in the media can be at various concentrations. The present invention provides that concentration is between 0.01 mg per liter to 10 mg per liter, such as 0.1, 0.5, 1, or 5 mg/L.

In particularly preferred embodiments, proliferation and elongation media contains benzyl adenine at a concentration ranging from 1.5 to 3 mg/L, preferably 1.5 mg/L, 2 mg/L, 2.5 mg/L, or 3 mg/L; and most preferably at 1.5 mg/L.

In other particularly preferred embodiments, the proliferation and elongation media contains indole butyric acid at a concentration ranging from 0.15 to 3.0 mg/L; preferably 0.15 mg/L, 0.5 mg/L, 1 mg/L, 2 mg/L, or 3 mg/L; and most preferably 0.15 mg/L.

Preferred compositions of proliferation and elongation media include 1.5 mg/L BA and 3.0 mg/L IBA, 1.5 mg/L BA and 0.15 mg/L IBA, or 3.0 mg/L BA and 0.2 mg/L IBA.

In preferred embodiments, the proliferation and elongation media contains 1.5 mg/L BA and 0.15 mg/L IBA.

Culture Conditions

In certain embodiments, the culture conditions (i.e., light cycle, light intensity, media, temperature, relative humidity) are the same throughout the initiation, proliferation and elongation, and rooting stages. Subculturing is performed as necessary; preferably, every 3 to 4 weeks.

Once well-formed roots are obtained, plantlets can be hardened on soil, sand, moss, charcoal or other media either alone or in combination in defined ratio. The plantlets can then be transferred to the fields by direct sowing or transplanting of the cuttings.

All references cited herein are hereby incorporated by reference.

The invention will be better understood by reference to the following Example.

Example

The following steps are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Step 1: Selecting the Healthy Mother Plants

Elite mother plants were selected on the basis of higher yield of leaf biomass and assessed for their size, weight, and general growth, appearance and absence of infection or contamination to decide requisite eliteness of the mother plant.

Step 2: Treating the Mother Plant:

The mother plants were decontaminated by spraying with Bavistin at a concentration of about 1%

Step 3: Isolating Explants from Elite Variety of Mother Plant

The shoots of a healthy elite mother Aloe plants from the field having high acemannan content were collected. Shoots were thoroughly washed under running water to remove dust adhering to it. Shoot tip explants were collected from off shoot-derived plants of the selected elite plant.

Step 4: Cleaning of the Explants:

The explants were washed thoroughly with tap water to remove soil adhered to it. The roots were then cut and the leaves carefully removed from the shoot tips. The explants were then dipped in 2% solution of TWEEN-20, for 10 minutes.

Step 5: Sterilizing the Explants by Primary and Secondary Sterilization:

The explants were sterilized by subjecting the cleaned explant to primary sterilization by treating the explants with a solution containing Bavistin 1% for 1 hr and then rinsing with sterile water. Each explant was washed and treated separately to avoid cross contamination.

Secondary sterilization was conducted in a laminar flow bench by shaking in 70% alcohol for 30 seconds and then thoroughly washing in autoclaved distilled water. The explants were then immersed in 0.1% mercuric chloride solution for 4 minutes, followed by a thorough rinse with sterile distilled water and again treated with 0.1% mercuric chloride solution for 4 minutes, followed by thorough rinsing in sterile distilled water for final preparation of the apical meristem explant for inoculation.

Step 6: Inoculating the Explants on Culture Initiation Medium to Give Multiple Shoots The explants were then given a fresh cut at the base and inoculated. For final preparation of meristematic explants for inoculation, the explant was trimmed by giving a fresh cut at the base without damaging the apical and axillary meristem, taking care to isolate only the meristematic tissue and not other tissues. To avoid contamination and resultant loss of valuable cultures, each explant was treated separately.

Micropropagation was conducted in three stages. The basal medium for all three stages was Murashige and Skoog's (1962) MS medium. The sterilized explants were inoculated in culture initiation medium with basal salts of MS medium and kept in suitable culture conditions to give multiple shoots.

The culture medium for initiation, proliferation and elongation, and rooting was Murashige & Skoog medium with full strength of the basal nutrients having 3% sucrose and solidified with 0.8% agar. In certain stages, the media was supplemented with hormones.

The culture conditions were 16 hours photoperiod at about 2000 lux light intensity followed by 8 hours of dark period. Temperature was kept constant at 22° C. to 24° C. and RH was maintained at about 60%.

Step 7: Transferring the Cultures to Proliferation and Elongation Media

Cultures were initiated separately in 25×150 mm borosilicate test tubes in plain MS media.

Multiple shoots were isolated and transferred into proliferation and elongation medium with MS medium containing the same basal salts as in the initiation medium and kept in growth room having predefined culture conditions favorable for the healthy development of the cultures. Proliferation was conducted in media containing benzyl adenine (BA) alone or BA in combination with indole butyric acid (IBA). Various concentration ranges were tried to optimize the most preferable concentration and combination of BA with IBA, as described below:

1, 1.5, or 3.0 mg/L BA alone 1.5 mg/L BA+0.15 mg/L IBA 3 mg/L BA+0.2 mg/L IBA

The best results were obtained with explants proliferated on media containing 1.5 mg/L BA and 0.15 mg/L IBA under the same culture conditions as in the initiation step. A multiplication of around 100 shoots were obtained in 4 months time when the explants were transferred to MS medium supplemented with 1.5 mg/L BA and 0.15 mg/L IBA.

The culture conditions were the same as those used for initiation. Elongated shoots were subcultured on proliferation and elongation medium at an interval of every 3 to 4 weeks. At all the stages, a monthly record of growth was maintained.

Step 8: Transferring the Elongated Shoots to Rooting Medium

Regenerated shoots were rooted in both media containing indole acetic acid (0.5, 1.0, or 2.0 mg/L LAA) and MS media lacking any hormones. Shoots were more successfully rooted in the MS media lacking hormones. The culture conditions were the same as those used for initiation.

Step 9: Subjecting In Vitro Grown Plantlets to Primary and Secondary Hardening.

Regenerated plants were hardened in a 50 cavity portrays having 1"×1"1.5" cavity size, in a greenhouse with a fan-pad cooling system and fogger to control temperature and relative humidity. The greenhouse temperature did not exceed 30 degrees Celsius. The maximum daylight intensity during hardening was 12000 to 14000 lux. Immediately after transfer to the greenhouse the plantlets were kept at 100% relative humidity for first 20 days and then at a RH of 50 to 60%. The substrate used for hardening of regenerated plantlets was 50:25:25 of sand: soil: fym. The plants were kept in the greenhouse for 30 days and then shifted to a shade house.

Step 10: Transfer of the Hardened Plantlets to Fields

The plants successfully transferred to the field were morphologically similar to mother plants Thus, the described method successfully uses a meristematic explant to give large number of true-to-type clones.

Summary of the Results

The multiplication ratio obtained by the above method was as high as 1:4. The success rate during rooting was up to 90% in media containing MS media lacking hormones and during hardening up to 80%. Regenerated plantlets transferred to the greenhouse showed 90% survival. When transferred to the shade house they showed 85% survival. Thus it is evident that the described methods have a very high success rate.

Culture initiation was noticed in hormone-free MS media after one week. Continued subculture in the same media did not produce further proliferation in shoots. However, when initiated cultures were transferred to media containing a combination of BA (1.5 mg/L) and IBA (0.15 mg/L), proliferation began within a month. A multiplication of around 100 shoots was obtained in 4 months time. No other treatment successfully induced healthy shoot bud formation. We noted a 2-fold increase in the number of shoot buds per subculture in 2 subcultures which later increased to a 4-fold increase. The average number of shoots per explant was 4.

Overall, the shoots inoculated in hormone free media showed 100% rooting in 3 weeks, whereas no rooting was observed in shoots inoculated in MS supplemented with IAA.

Thus a micropropagation method using initiation medium lacking hormones, proliferation and elongation medium containing BA with IBA and rooting medium lacking hormones is useful for mass multiplication of *Aloe vera* plants.

In particular, a micropropagation method using meristematic tissue as an explant in hormone-free media in initiation and rooting giving a number of multiple shoots in the range of 3-4 shoots per explants and high success rate during rooting and hardening renders the present invention process commercially viable for in vitro mass culture of *Aloe vera* for large-scale multiplication of the true-to-type clones of elite variety.

While we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, are within the scope of the invention.

We claim:

1. A method for producing a true-to-type clone of an *Aloe barhadensis* mother plant having acemannan content between 9.9% and 12.1% in a hormone free initiation and rooting medium comprising the steps of:
    a) isolating a meristematic explant from said mother plant;
    b) culturing said meristematic explant in a hormone free initiation medium to generate shoots;
    c) culturing said shoots in proliferation and elongation medium comprising benzyladenine (BA) and indole butyric acid (IBA) to generate elongated shoots;
    d) culturing said elongated shoots in a hormone free MS solidified rooting medium to generate plantlets; and
    e) culturing said plantlets to produce a true-to-type clone of said *Aloe barbadensis* mother plant.

2. The method of claim 1, wherein said benzyl adenine is at a concentration selected from the group consisting of: 1.5 mg/L, 2 mg/L, 2.5 mg/L, and 3 mg/L.

3. The method of claim 2, wherein said benzyl adenine is at a concentration of about 1.5 mg/L.

4. The method of claim 1, wherein said indole butyric acid is at a concentration selected from the group consisting of: 0.15 mg/L, 0.5 mg/L, 1 mg/L, 2 mg/L, and 3 mg/L.

5. The method of claim 4, wherein said indole butyric acid is at a concentration of about 0.15 mg/L.

6. The method of claim 1, wherein said meristematic explant is from a shoot tip or a nodal bud.

7. The method of claim 4, wherein said meristematic explant is from a shoot tip.

* * * * *